(12) United States Patent
Penner et al.

(10) Patent No.: US 7,756,587 B2
(45) Date of Patent: ***Jul. 13, 2010

(54) SYSTEMS AND METHODS FOR COMMUNICATING WITH IMPLANTABLE DEVICES

(75) Inventors: Avi Penner, Tel Aviv (IL); Eyal Doron, Kiryat Yam (IL)

(73) Assignee: Cardiac Pacemakers, Inc., St. Paul, MN (US)

( * ) Notice: Subject to any disclaimer, the term of this patent is extended or adjusted under 35 U.S.C. 154(b) by 483 days.

This patent is subject to a terminal disclaimer.

(21) Appl. No.: 11/876,620

(22) Filed: Oct. 22, 2007

(65) Prior Publication Data

US 2008/0103553 A1     May 1, 2008

Related U.S. Application Data

(63) Continuation of application No. 11/276,576, filed on Mar. 6, 2006, now Pat. No. 7,617,001, which is a continuation of application No. 09/989,912, filed on Nov. 19, 2001, now Pat. No. 7,024,248, which is a continuation-in-part of application No. 09/690,015, filed on Oct. 16, 2000, now Pat. No. 6,628,989.

(51) Int. Cl.
*A61N 1/18* (2006.01)

(52) U.S. Cl. ............................ 607/60; 607/30; 607/32
(58) Field of Classification Search ......... 128/897–899, 128/903–904; 607/29–34, 59–61
See application file for complete search history.

(56) References Cited

U.S. PATENT DOCUMENTS 2,786,899 A    3/1957   Carlisle
3,536,836 A   10/1970   Pfeiffer (Continued)

FOREIGN PATENT DOCUMENTS

EP            0 499 939         8/1992

(Continued)

OTHER PUBLICATIONS

Y. Porat, et al., "Method for Transfer of Energy to an Electronic Circuit Implanted in a Living Body and a Device for Such Method", PCT Publication No. WO 98/43338, Oct. 1, 1998.

(Continued)

*Primary Examiner*—Carl H Layno
*Assistant Examiner*—Jessica Sarcione
(74) *Attorney, Agent, or Firm*—Faegre & Benson LLP (57) ABSTRACT

Systems and methods for communicating with an implant within a patient's body using acoustic telemetry includes an external communications device attachable to the patient's skin. The device includes an acoustic transducer for transmitting acoustic signals into the patient's body and/or for receiving acoustic signals from the implant. The device includes a battery for providing electrical energy to operate the device, a processor for extracting data from acoustic signals received from the implant, and memory for storing the data. The device may include an interface for communicating with a recorder or computer, e.g., to transfer data from the implant and/or to receive instructions for controlling the implant. The device is secured to the patient's skin for controlling, monitoring, or otherwise communicating with the implant, while allowing the patient to remain mobile.

20 Claims, 4 Drawing Sheets

U.S. PATENT DOCUMENTS

| | | |
|---|---|---|
| 3,672,352 A | 6/1972 | Summers |
| 3,757,770 A | 9/1973 | Brayshaw et al. |
| 3,805,796 A | 4/1974 | Terry, Jr. et al. |
| 3,853,117 A | 12/1974 | Murr |
| 3,943,915 A | 3/1976 | Severson |
| 3,970,987 A | 7/1976 | Kolm |
| 4,026,276 A | 5/1977 | Chubbuck |
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |
| 4,281,666 A | 8/1981 | Cosman |
| 4,281,667 A | 8/1981 | Cosman |
| 4,340,038 A | 7/1982 | McKean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A | 6/1986 | Snell et al. |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,708,127 A | 11/1987 | Abdelghani |
| 4,719,919 A | 1/1988 | Marchosky et al. |
| 4,791,915 A | 12/1988 | Barsotti et al. |
| 4,791,936 A | 12/1988 | Snell et al. |
| 4,793,825 A | 12/1988 | Benjamin et al. |
| 4,869,251 A | 9/1989 | Lekholm et al. |
| 4,885,002 A | 12/1989 | Watanabe et al. |
| 4,911,217 A | 3/1990 | Dunn et al. |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,184,605 A | 2/1993 | Grzeszykowski |
| 5,218,861 A | 6/1993 | Brown et al. |
| 5,279,292 A | 1/1994 | Baumann et al. |
| 5,291,899 A | 3/1994 | Watanabe et al. |
| 5,381,067 A | 1/1995 | Greenstein et al. |
| 5,423,334 A | 6/1995 | Jordan |
| 5,433,736 A | 7/1995 | Nilsson |
| 5,445,150 A | 8/1995 | Dumoulin et al. |
| 5,495,453 A | 2/1996 | Wociechowski et al. |
| 5,562,621 A | 10/1996 | Claude et al. |
| 5,619,997 A | 4/1997 | Kaplan |
| 5,620,475 A | 4/1997 | Magnusson |
| 5,704,352 A | 1/1998 | Tremblay et al. |
| 5,704,366 A | 1/1998 | Tacklind et al. |
| 5,712,917 A | 1/1998 | Offutt |
| 5,721,886 A | 2/1998 | Miller |
| 5,724,985 A | 3/1998 | Snell et al. |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A | 6/1998 | Snell et al. |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,891,180 A | 4/1999 | Greeninger et al. |
| 5,904,708 A | 5/1999 | Goedeke |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,030,374 A | 2/2000 | McDaniel |
| 6,070,103 A | 5/2000 | Ogden |
| 6,140,740 A | 10/2000 | Porat et al. |
| 6,141,588 A | 10/2000 | Cox |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,176,840 B1 | 1/2001 | Nishimura et al. |
| 6,183,426 B1 | 2/2001 | Akisada et al. |
| 6,185,452 B1 | 2/2001 | Schulman et al. |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,261,249 B1 | 7/2001 | Tallish et al. |
| 6,277,078 B1 | 8/2001 | Porat et al. |
| 6,315,721 B2 | 11/2001 | Schulman et al. |
| 6,431,175 B1 | 8/2002 | Penner et al. |
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 | 10/2002 | Ferek-Petric |
| 6,564,807 B1 | 5/2003 | Schulman et al. |
| 6,577,899 B2 | 6/2003 | Lebel et al. |
| 6,584,352 B2 | 6/2003 | Combs et al. |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,676,601 B1 | 1/2004 | Lacoste |
| 6,689,091 B2 | 2/2004 | Bui et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,790,187 B2 | 9/2004 | Thompson et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |

| | | |
|---|---|---|
| 7,013,178 B2 | 3/2006 | Reinke et al. |
| 7,024,248 B2 | 4/2006 | Penner et al. |
| 7,027,871 B2 | 4/2006 | Burnes et al. |
| 7,027,872 B2 | 4/2006 | Thompson |
| 7,035,684 B2 | 4/2006 | Lee |
| 7,060,030 B2 | 6/2006 | Von Arx et al. |
| 7,061,381 B2 | 6/2006 | Forcier et al. |
| 7,082,334 B2 | 7/2006 | Boute et al. |
| 7,096,068 B2 | 8/2006 | Mass et al. |
| 7,123,964 B2 | 10/2006 | Betzold et al. |
| 7,198,603 B2 | 4/2007 | Penner et al. |
| 7,203,551 B2 | 4/2007 | Houben et al. |
| 7,209,790 B2 | 4/2007 | Thompson et al. |
| 7,212,133 B2 | 5/2007 | Goetz et a |
| 7,236,821 B2 | 6/2007 | Cates et al. |
| 7,273,457 B2 | 9/2007 | Penner et al. |
| 7,283,874 B2 | 10/2007 | Penner et al. |
| 7,286,872 B2 | 10/2007 | Kramer et al. |
| 7,319,903 B2 | 1/2008 | Bange et al. |
| 7,335,161 B2 | 2/2008 | Von Arx et al. |
| 7,353,063 B2 | 4/2008 | Simms, Jr. |
| 7,469,161 B1 | 12/2008 | Gandhi et al. |
| 7,479,108 B2 | 1/2009 | Rini et al. |
| 7,617,001 B2 * | 11/2009 | Penner et al. .................. 607/60 |
| 2001/0025139 A1 | 9/2001 | Pearlman |
| 2002/0045921 A1 | 4/2002 | Wolinsky et al. |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2003/0114897 A1 | 6/2003 | Von Arx et al. |
| 2003/0212441 A1 | 11/2003 | Starkweather et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0172083 A1 | 9/2004 | Penner |
| 2004/0210141 A1 | 10/2004 | Miller |
| 2005/0113705 A1 | 5/2005 | Fischell et al. |
| 2005/0159785 A1 | 7/2005 | Rueter |
| 2005/0159789 A1 | 7/2005 | Brockway et al. |
| 2005/0288727 A1 | 12/2005 | Penner |
| 2006/0009818 A1 | 1/2006 | Von Arx et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0064134 A1 | 3/2006 | Mazar et al. |
| 2006/0064135 A1 | 3/2006 | Brockway |
| 2006/0064142 A1 | 3/2006 | Chavan et al. |
| 2006/0085039 A1 | 4/2006 | Hastings et al. |
| 2006/0122667 A1 | 6/2006 | Chavan et al. |
| 2006/0142819 A1 | 6/2006 | Penner et al. |
| 2006/0149329 A1 | 7/2006 | Penner |
| 2007/0010742 A1 | 1/2007 | Torp et al. |
| 2007/0142728 A1 | 6/2007 | Penner et al. |
| 2007/0150014 A1 | 6/2007 | Kramer et al. |
| 2007/0162090 A1 | 7/2007 | Penner |
| 2007/0179549 A1 | 8/2007 | Russie |
| 2007/0250126 A1 | 10/2007 | Maile et al. |
| 2008/0071178 A1 | 3/2008 | Greenland et al. |
| 2008/0108915 A1 | 5/2008 | Penner |
| 2008/0171941 A1 | 7/2008 | Huelskamp et al. |
| 2008/0195002 A1 | 8/2008 | Thompson et al. |

FOREIGN PATENT DOCUMENTS

| | | |
|---|---|---|
| EP | 0 928 598 | 12/1998 |
| WO | WO88/02250 | 4/1988 |
| WO | WO 98/43338 | 10/1998 |
| WO | WO 99/34453 | 7/1999 |
| WO | WO 00/47109 | 8/2000 |
| WO | WO 01/28627 A1 | 4/2001 |
| WO | WO 01/74278 A2 | 10/2001 |
| WO | WO01/97907 | 12/2001 |
| WO | WO 02/03347 | 1/2002 |
| WO | WO03/002243 | 1/2003 |
| WO | WO03/096889 | 11/2003 |
| WO | WO2005/009535 | 2/2005 |
| WO | WO2005/053786 | 6/2005 |
| WO | WO2006/060668 | 6/2006 |
| WO | WO2007/070794 | 6/2007 |
| WO | WO2007/080487 | 7/2007 |
| WO | WO2007/127696 | 11/2007 |
| WO | WO2008/118908 | 10/2008 |

OTHER PUBLICATIONS

M.M. Friedman, "Piezoelectric Transducer", PCT Publication No. WO 99/34453, Jul. 8, 1999.

Lone Wolinsky, et al., U.S. Appl. No. 2002/045921 A1, Apr. 18, 2002.

Harrison et al., "A Low-Power Low-Noise CMOS Amplifier for Neural Recording Applications," IEEE Journal of Solid-State Circuits 38(6):958-965, Jun. 2003.

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): 1-14, Mar. 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydroceplhalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

* cited by examiner

SYSTEMS AND METHODS FOR COMMUNICATING WITH IMPLANTABLE DEVICES

CROSS-REFERENCE TO RELATED APPLICATIONS

This application is a continuation of U.S. application Ser. No. 11/276,576, filed Mar. 6, 2006 (now U.S. Pat. No. 7,617, 001), which is a continuation of U.S. application Ser. No. 09/989,912, filed Nov. 19, 2001 (now U.S. Pat. No. 7,024, 248) which is a continuation-in-part of U.S. application Ser. No. 09/690,015, filed Oct. 16, 2000 (now U.S. Pat. No. 6,628, 989). All of these applications are expressly incorporated herein by reference.

FIELD OF THE INVENTION

The present invention relates generally to systems and methods for measuring physiological conditions and/or performing therapeutic functions within a patient's body, particularly to systems and methods for controlling and/or energizing devices that may be implanted within a body, and more particularly to implants that may be energized, activated, controlled, and/or otherwise communicate via acoustic energy.

BACKGROUND OF THE INVENTION

Devices are known that may be implanted within a patient's body for monitoring one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like.

Often it is desirable to communicate with such devices once they are implanted within a patient by external command, for example, to obtain data, and/or to activate or otherwise control the implant. An implant may include wire leads from the implant to an exterior surface of the patient, thereby allowing an external controller or other device to be directly coupled to the implant. Alternatively, the implant may be remotely controlled, e.g., using an external induction device. For example, an external radio frequency (RF) transmitter may be used to communicate with the implant. RF energy, however, may only penetrate a few millimeters into a body, because of the body's dielectric nature, and therefore may not be able to communicate effectively with an implant that is located deep within the body. In addition, although an RF transmitter may be able to induce a current within an implant, the implant's receiving antenna, generally a low impedance coil, may generate a voltage that is too low to provide a reliable switching mechanism.

In a further alternative, electromagnetic energy may be used to control an implant, since a body generally does not attenuate magnetic fields. The presence of external magnetic fields encountered by the patient during normal activity, however, may expose the patient to the risk of false positives, i.e., accidental activation or deactivation of the implant. Furthermore, external electromagnetic systems may be cumbersome and may not be able to effectively transfer coded information to an implant.

Accordingly, systems and methods for communicating with an implant that may be implanted within a patient's body, such as a pressure sensor, a drug delivery device, a pacemaker, or a nerve stimulator, would be considered useful.

SUMMARY OF THE INVENTION

The present invention is generally directed to systems and methods for communicating with implants or other devices that are placed, e.g., using open surgical or minimally invasive techniques, within a mammalian body. The implant may include one or more sensors for monitoring pressure or other physiological parameters and/or may perform one or more therapeutic functions. More particularly, the present invention is directed to external systems for controlling, activating, energizing, and/or otherwise communicating with such implants using acoustic telemetry, and to methods for using such systems.

In accordance with one aspect of the present invention, a system is provided for communicating with an implant within a body that includes an external communications device, e.g., a controller, securable to an exterior surface of a patient's body. Preferably, the controller is sufficiently small and portable that it may remain secured to the patient, possibly for extended time periods. For example, the device may be attached to or within a patch that may be secured to a patient's skin.

In one embodiment, the device is an external controller that generally includes one or more acoustic transducers, including a first acoustic transducer, for transmitting one or more acoustic signals into the patient's body. The controller may also include an energy source for powering the one or more acoustic transducers, and/or a processor or other electrical circuit for controlling operation of the controller. In addition, one or more of the acoustic transducers, such as the first acoustic transducer, may be configured for receiving acoustic signals from an implant within the patient's body. The controller may include memory for storing data, and the processor may extract sensor data and/or other data from acoustic signals received from an implant, e.g., for storage in the memory. In addition, the controller may include a connector, lead, transmitter, receiver, or other interface for communicating with a recorder or other electronic device, such as a computer, personal digital assistant, or a wireless device, such as a cellular phone. The controller may be coupled to such an electronic device for transferring sensor data or other data stored in the memory of the controller and/or for receiving instructions or commands from the electronic device.

In addition, the system may include an implant for placement within the patient's body. The implant may include an electrical circuit for performing one or more commands when the implant is activated, an energy storage device, and/or one or more acoustic transducers, e.g., a second acoustic transducer, coupled to the electrical circuit and/or the energy storage device. Optionally, the electrical circuit may include a switch coupled to the energy storage device and/or the second acoustic transducer. The second acoustic transducer may receive one or more acoustic signals from the first acoustic transducer of the external device. For example, the switch may be closed and/or opened in response to a first acoustic signal to begin or discontinue current flow from the energy storage device to the electrical circuit or other components of the implant.

In a preferred embodiment, the external controller's processor controls the first acoustic transducer to transmit a first acoustic signal and/or a second acoustic signal. The switch of the implant may be closed when the first acoustic signal is received by the second acoustic transducer, while the switch may be opened when the second acoustic signal is received by the second acoustic transducer. In addition or alternatively, the first acoustic transducer may transmit first and second acoustic signals separated by a delay. The switch may be closed and/or opened only when the second acoustic transducer receives the first and second acoustic signals separated by a predetermined delay, thereby minimizing the risk of accidental activation or deactivation of the implant.

In yet another alternative, the first acoustic transducer may transmit a first acoustic signal, e.g., an activation signal, followed by a second acoustic signal, e.g., including a set of commands. The second acoustic transducer may receive the first and second acoustic signals, and the electrical circuit of the implant may extract the set of commands from the second acoustic signal, and control operation of the implant as instructed by the set of commands. In a further alternative, the implant may run continuously or intermittently, and the external controller may control, monitor, energize, and/or program the implant using acoustic telemetry during operation of the implant.

In an exemplary embodiment, the implant may include a sensor coupled to the electrical circuit, and the one or more commands may include measuring a physiological parameter within the body using the sensor. The second acoustic transmitter may transmit one or more acoustic signals including sensor data indicating the physiological parameter to the controller. In an alternative embodiment, the implant may be coupled to a therapeutic device or may include an internal therapeutic device coupled to the electrical circuit. The electrical circuit may control the therapeutic device in response to a physiological parameter measured by the sensor or in response to acoustic signals received from the external controller. For example, the implant may include a pacemaker that may be implanted via a minimally invasive catheter-based procedure. Any programming and/or interrogation of the pacemaker may be accomplished using acoustic telemetry from the external controller. In yet another alternative embodiment, the implant may include an actuator coupled to the electrical circuit, and the one or more commands may include activating the actuator to control a therapeutic device coupled to the actuator, such as a nerve stimulator or a controlled delivery drug release system.

In addition, the energy storage device of the implant may include a rechargeable device, such as a capacitor or a battery. For this embodiment, the system may include an external charger that may include a probe configured for placement against an exterior of the patient's body. The charger may include a source of electrical energy, such as a radio frequency (RF) generator, that is coupled to the probe. The probe may include another acoustic transducer, e.g., a third acoustic transducer, for converting electrical energy from the source of electrical energy into acoustic energy. The third acoustic transducer may transmit acoustic signals including acoustic energy into the patient's body. One or more acoustic transducers of the implant, e.g., the second acoustic transducer, may be configured for converting these acoustic signals into electrical energy for recharging the energy storage device and/or powering the implant.

Thus, a system in accordance with the present invention may include an external controller that has sufficient power to control its own operation and to communicate with the implant. Because of its limited energy requirements, however, the controller may be relatively small and portable, e.g., may be attached to the patient, while still allowing the patient to engage in normal physical activity. The controller may be used to communicate with an implant, e.g., periodically activating or deactivating the implant, and/or recording data generated and transmitted by the implant. Because it is located outside the patient's body, the controller may be more easily programmed or reprogrammed than the implant, and/or may be repaired or replaced if necessary without requiring an interventional procedure.

In addition, the system may include a separate external charger that includes a substantially more powerful energy source, enabling it to recharge the energy storage device of the implant. For this reason, unlike the external controller, the charger may be a relatively bulky device that may include a portable probe for contacting the patient's skin, and a large energy generator or converter that is stationary or of limited mobility. In an alternative embodiment, the external controller and charger may be provided as a single device, e.g., including one or more acoustic transducers and/or one or more processors for performing the functions of both devices, as described above. In this embodiment, however, portability of the system and convenience to the patient may be compromised.

Other objects and features of the present invention will become apparent from consideration of the following description taken in conjunction with the accompanying drawings.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
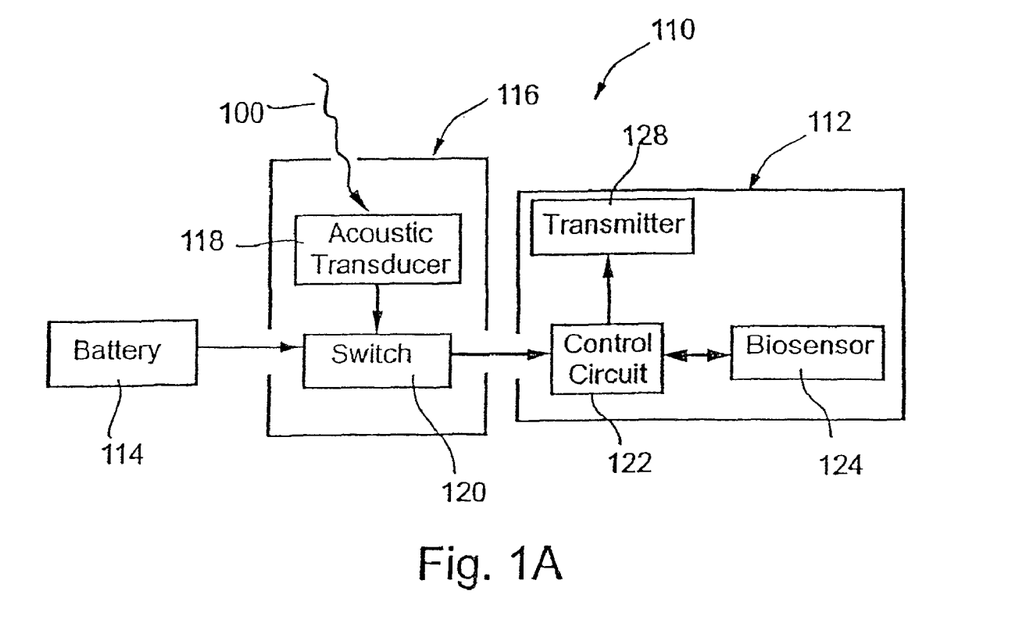
FIGS. 1A-1C are schematic drawings, showing exemplary embodiments of an implant, in accordance with the present invention.
Figure 1B:
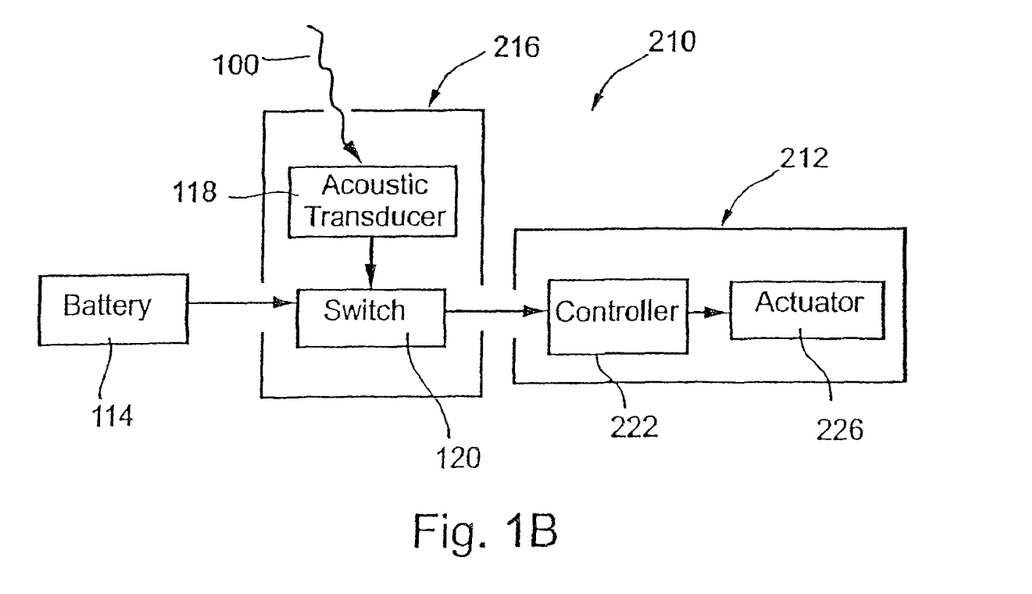
Figure 1C:
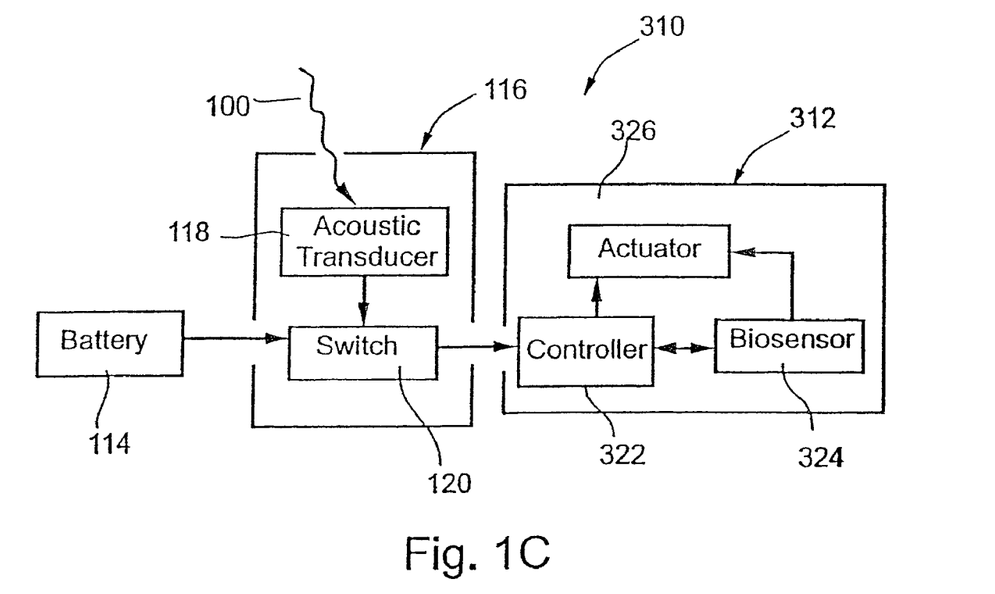

Turning to the drawings, FIGS. 1A-1C schematically show several exemplary embodiments of an implant 110, 210, 310, in accordance with the present invention. Generally, the implant 110, 210, 310 includes an electrical circuit 112, 212, 312 configured for performing one or more functions or commands when the implant 110, 210, 310 is activated, as described further below. In addition, the implant 110, 210, 310 includes an energy storage device 114 and optionally may include a switch 116 coupled to the electrical circuit 112, 212, 312 and the energy storage device 114. The switch 116 may be activated upon acoustic excitation 100 from an external acoustic energy source (not shown) to allow current flow from the energy storage device 114 to the electrical circuit 112, 212, 312.

In a preferred embodiment, the switch 116 includes an acoustic transducer 118, such as that disclosed in PCT Publication No. WO 99/34,453, published Jul. 8, 1999, or in U.S. application Ser. No. 09/888,272, filed Jun. 21, 2001, the disclosures of which are expressly incorporated herein by reference. In addition, the switch 116 also includes a switch circuit 120, such as switch circuit 400 shown in FIG. 2, although alternatively other switches, such as a miniature electromechanical switch and the like (not shown) may be provided. In a further alternative, the acoustic transducer 118 may be coupled to the electrical circuit 112, 212, 312 and/or the energy storage device 114, and the switch circuit 120 may be eliminated.

The energy storage device 114 may be any of a variety of known devices, such as an energy exchanger, a battery and/or a capacitor (not shown). Preferably, the energy storage device 114 is capable of storing electrical energy substantially indefinitely for as long as the acoustic switch 116 remains open, i.e., when the implant 110, 210, 310 is in a "sleep" mode. In addition, the energy storage device 114 may be capable of being charged from an external source, e.g., inductively using acoustic telemetry, as will be appreciated by those skilled in the art. In a preferred embodiment, the energy storage device 114 includes both a capacitor and a primary, non-rechargeable battery. Alternatively, the energy storage device 114 may include a secondary, rechargeable battery and/or capacitor that may be energized before activation or use of the implant 110, 210, 310.

The implant 110, 210, 310 may be surgically or minimally invasively inserted within a human body in order to carry out a variety of monitoring and/or therapeutic functions. For example, the electrical circuit 112, 212, 312 may include a control circuit 122, 222, 322, a biosensor 124, 324, an actuator 226, 326, and/or a transmitter 128, as explained in application Ser. No. 09/690,015, incorporated by reference above. The implant 210, 310 may be configured for providing one or more therapeutic functions, for example, to activate and/or control a therapeutic device implanted within a patient's body, such as an atrial defibrillator or pacemaker, a pain relief stimulator, a neuro-stimulator, a drug delivery device, and/or a light source used for photodynamic therapy. Alternatively, the implant may be used to monitor a radiation dose including ionizing, magnetic and/or acoustic radiation, to monitor flow in a bypass graft, to produce cell oxygenation and membrane electroporation, and the like. In addition or alternatively, the implant 110 may be used to measure one or more physiological parameters within the patient's body, such as pressure, temperature, electrical impedance, position, strain, pH, and the like.

The implant may operate in one of two modes, a "sleep" or "passive" mode when the implant remains dormant and not in use, i.e., when the acoustic switch 116 is open, and an "active" mode, when the acoustic switch 116 is closed, and electrical energy is delivered from the energy storage device 114 to the electrical circuit 112, 212, 312. Alternatively, the implant may operate continuously or intermittently. Because the acoustic switch 116 is open in the sleep mode, there is substantially no energy consumption from the energy storage device 114, and consequently, the implant may remain in the sleep mode virtually indefinitely, i.e., until activated. Thus, an implant in accordance with the present invention may be more energy efficient and, therefore, may require a relatively small energy storage device than implants that continuously draw at least a small amount of current in their "passive" mode.

Turning to FIG. 1A, a first preferred embodiment of an implant 110 is shown in which the electrical circuit 112 includes a control circuit 122, a biosensor 124 coupled to the controller 122, and a transmitter 128 coupled to the control circuit 122. The controller 122 may include circuitry for activating or controlling the biosensor 124, for receiving signals from the biosensor 124, and/or for processing the signals into data, for example, to be transmitted by the transmitter 128. Optionally, the electrical circuit 112 may include memory (not shown) for storing the data. The transmitter 128 may be any device capable of transmitting data from the control circuit 122 to a remote location outside the body, such as an acoustic transmitter, a radio frequency transmitter, and the like. Preferably, the control circuit 122 is coupled to the acoustic transducer 118 such that the acoustic transducer 118 may be used as a transmitter 128, as well as a receiver, instead of providing a separate transmitter.

The biosensor 124 may include one or more sensors capable of measuring physiological parameters, such as pressure, temperature, electrical impedance, position, strain, pH, fluid flow, electrochemical sensor, and the like. Thus, the biosensor 124 may generate a signal proportional to a physiological parameter that may be processed and/or relayed by the control circuit 122 to the transmitter 128, which, in turn, may generate a transmission signal to be received by a device outside the patient's body. Data regarding the physiological parameter(s) may be transmitted continuously or periodically until the acoustic switch 116 is deactivated, or for a fixed predetermined time, as will be appreciated by those skilled in the art.

Turning to FIG. 1B, a second preferred embodiment of an implant 210 is shown in which the electrical circuit 212 includes a control circuit 222 and an actuator 226. The actuator 226 may be coupled to a therapeutic device (not shown) provided in or otherwise coupled to the implant 210, such as a light source, a nerve stimulator, a defibrillator, an electrochemical oxidation/reduction electrode, or a valve communicating with an implanted drug reservoir (in the implant or otherwise implanted within the body in association with the implant).

When the switch 120 is closed, the control circuit 222 may activate the actuator 226 using a pre-programmed protocol, e.g., to complete a predetermined therapeutic procedure, whereupon the switch 120 may automatically open, or the controller 222 may follow a continuous or looped protocol until the switch 120 is deactivated. Alternatively, the acoustic transducer 118 may be coupled to the control circuit 222 for communicating a new or unique set of commands to the control circuit 222. For example, a particular course of treatment for a patient having the implant 210 may be determined, such as a flow rate and duration of drug delivery, drug activation, drug production, or an energy level and duration of electrical stimulation. Acoustic signals including commands specifying this course of treatment may be transmitted from an external controller (not shown), as described below, to the acoustic switch 116, e.g., along with or subsequent to the activation signal 100. The control circuit 222 may interpret these commands and control the actuator 226 accordingly to complete the course of treatment.

Turning to FIG. 1C, yet another preferred embodiment of an implant 310 is shown in which the electrical circuit 312 includes a control circuit 322, a biosensor 324, and an actuator 326, all of which may be coupled to one another. This embodiment may operate similarly to the embodiments described above, e.g., to obtain data regarding one or more physiological parameters and/or to control a therapeutic device. In addition, once activated, the control circuit 322 may control the actuator 326 in response to data obtained from the biosensor 324 to control or adjust automatically a course of treatment being provided by a device connected to the actuator 326. For example, the actuator 326 may be coupled to an insulin pump (not shown), and the biosensor 324 may measure glucose levels within the patient's body. The control circuit 322 may control the actuator to open or close a valve on the insulin pump to adjust a rate of insulin delivery based upon glucose levels measured by the biosensor 324 in order to maintain the patient's glucose within a desired range.

Figure 2:
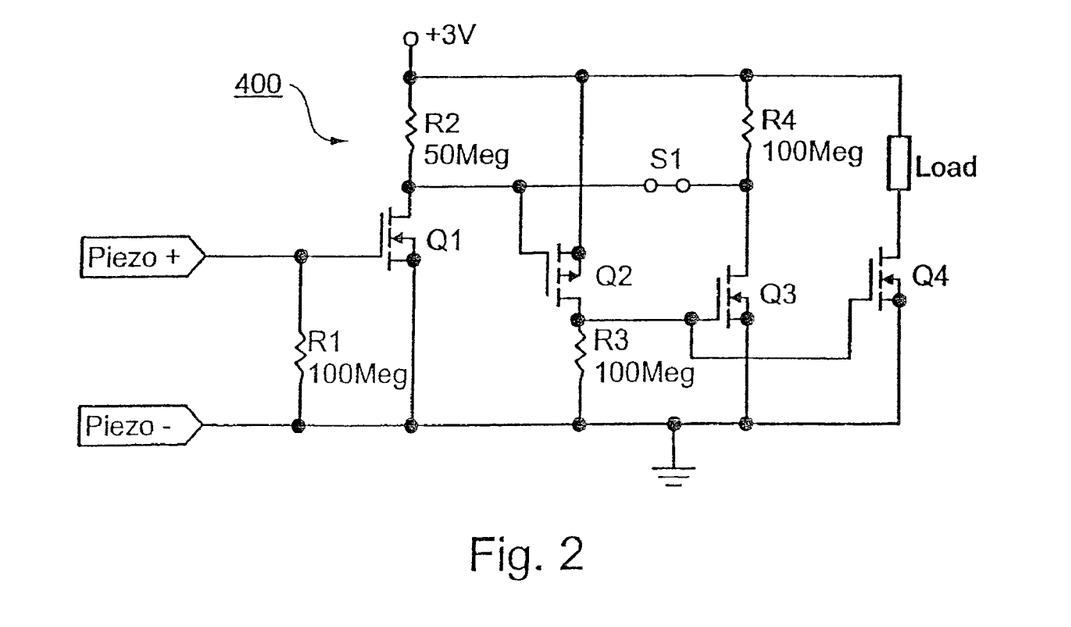
FIG. 2 is a schematic of an exemplary circuit for use as an acoustic switch, in accordance with the present invention.

Turning to FIG. 2, a preferred embodiment of a switch 400 is shown that may be incorporated into an implant in accordance with the present invention. The switch 400 includes a piezoelectric transducer, or other acoustic transducer (not shown, but generally connected to the switch 400 at locations piezo + and piezo −), a plurality of MOSFET transistors (Q1-Q4) and resistors (R1-R4), and switch S1. A "load" may be coupled to the switch 400, such as one of the electrical circuits described above. In the switch's "sleep" mode, all of the MOSFET transistors (Q1-Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit. Therefore, although an energy storage device (not shown, but coupled between the hot post, labeled with an exemplary voltage of +3V, and ground) is connected to the switch 400, no current is being drawn therefrom since all of the transistors are quiescent.

When the acoustic transducer of the implant detects an external acoustic signal, e.g., having a particular frequency, such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct current through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct current through resistor R4 and main switching transistor Q4 begins to conduct current through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3, & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open the switch 400, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, the switch 400 returns to its sleep mode, even if switch S1 is again closed. The switch 400 will only return to its active mode upon receiving a new acoustic activation signal from the piezoelectric transducer.

It should be apparent to one of ordinary skill in the art that the above-mentioned electrical circuit is not the only possible implementation of a switch for use with the present invention. For example, the switching operation may be performed using a CMOS circuit, which may draw less current when switched on, an electromechanical switch, and the like.

Figure 3:
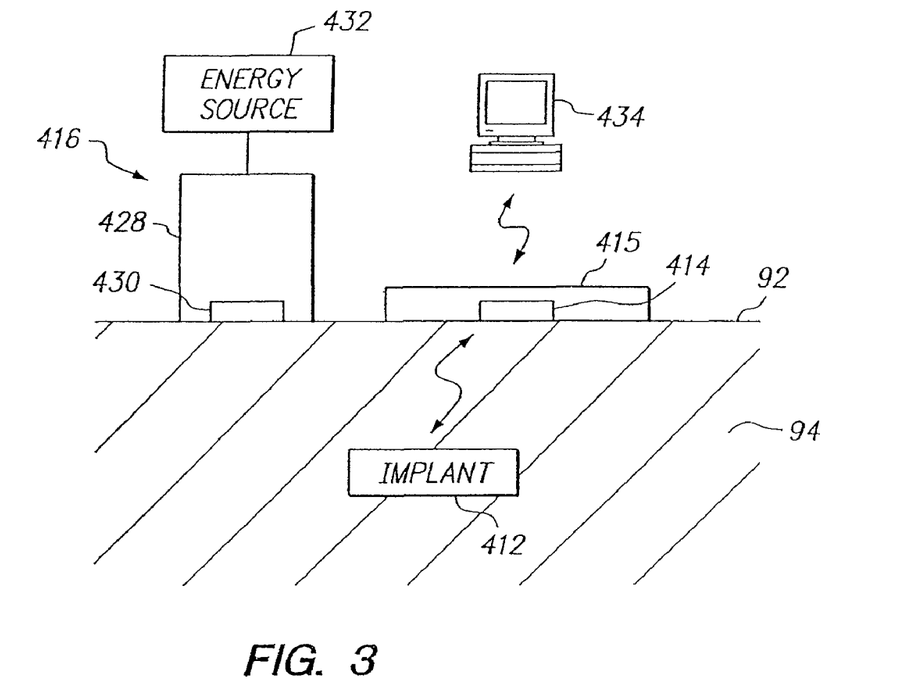
FIG. 3 is a cross-sectional view of a patient's body, showing a system for communicating with an implant, in accordance with the present invention.
Figure 4:
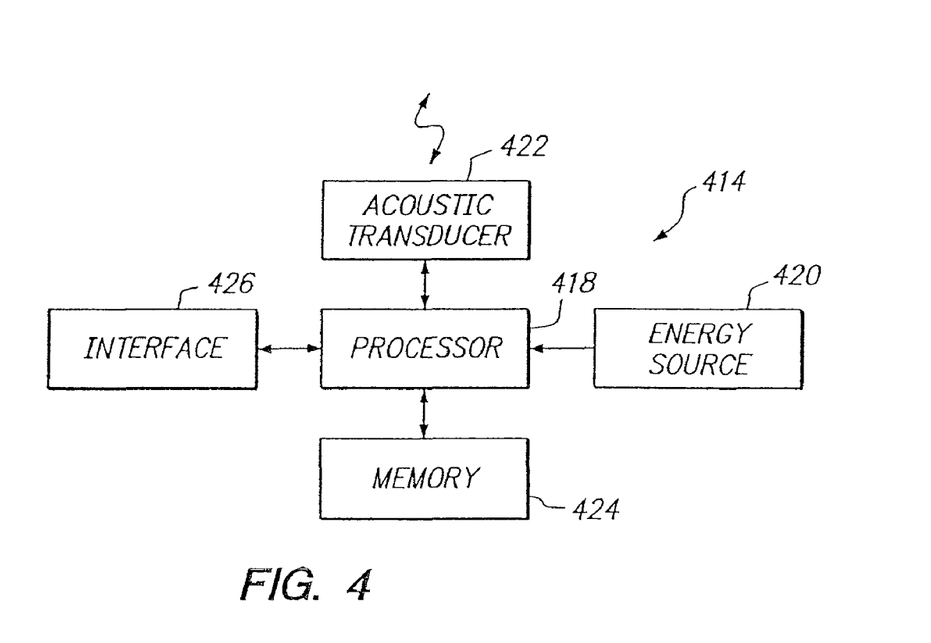
FIG. 4 is a schematic of an external controller for communicating with an implant, such as that shown in FIG. 3, in accordance with the present invention.

Turning to FIGS. 3 and 4, a system 410 is shown for communicating with an implant 412, such as one of those described above. Generally, the system 410 includes an external communications device or controller 414, and may include a charger 416, one or more implants 412 (only one shown for simplicity), and an external recorder, computer, or other electronic device 434.

With particular reference to FIG. 4, the external controller 414 may include a processor or other electrical circuit 418 for controlling its operation, and an energy source 420, e.g., a nonrechargeable or a rechargeable battery, coupled to the processor 418 and/or other components of the controller 414, such as a power amplifier or an oscillator (not shown). In addition, the controller 414 may include one or more acoustic transducers 422 that are configured for converting between electrical energy and acoustic energy, similar to those described above. As shown, a single acoustic transducer 422 is provided that may communicate using acoustic telemetry, i.e., capable both of converting electrical energy to acoustic energy to transmit acoustic signals, and converting acoustic energy to electrical energy to receive acoustic signals, as explained further below. Alternatively, separate and/or multiple acoustic transducers may be provided for transmitting and receiving acoustic signals.

In a preferred embodiment, the controller 414 also includes memory 424 coupled to the processor 418, e.g., for storing data provided to the controller 414, as explained further below. The memory 424 may be a temporary buffer that holds data before transfer to another device, or non-volatile memory capable of storing the data substantially indefinitely, e.g., until extracted by the processor 418 or other electronic device. For example, the memory 424 may be a memory card or an eprom (not shown) built into the controller 414 or otherwise coupled to the processor 418. The controller 414 may also include an interface 426, such as a lead or connector, or a transmitter and/or receiver, that may communicate with the external electronic device, as explained further below.

Preferably, the controller 414 is carried by a patch 415 that may be secured to a patient, e.g., to the patient's skin 92. For example, the patch 415 may include one or more layers of substantially flexible material to which the controller 414 and/or its individual components are attached. The patch 415 may include a single flexible membrane (not shown) to which the controller 414 is bonded or otherwise attached, e.g., using a substantially permanent adhesive, which may facilitate the patch 415 conforming to a patient's anatomy. Alternatively, the controller 414 may be secured between layers of material, e.g., within a pouch or other compartment (not shown) within the patch 415. For example, the patch 415 may include a pair of membranes (not shown) defining the pouch or compartment. The space within which the controller 414 is disposed may be filled with material to acoustically couple the acoustic transducer(s) (formed, for example, from PZT, composite PZT, Quartz, PVDF, and/or other piezoelectric material) of the controller 414 to an outer surface of the patch 415. Alternatively, the acoustic transducer(s) may be exposed, e.g., in a window formed in a wall of the patch 415.

The patch 415 may be formed from a flexible piezoelectric material, such as PVDF or a PVDF copolymer. Such polymers may allow the patch 415 to produce ultrasonic waves, as well as allowing the controller 414 to be secured to the patient's skin 92. Thus, the wall of the patch 415 itself may provide an acoustic transducer for the controller 414, i.e., for transmitting acoustic energy to and/or receiving acoustic energy from the implant 412.

The patch 415 may then be secured to the patient's skin 92 using a material, such as a layer of adhesive (not shown), substantially permanently affixed or otherwise provided on a surface of the patch. The adhesive may be hydrogel, silicon, polyurethane, polyethylene, polypropylene, fluorocarbon polymer, and the like. Alternatively, a separate adhesive may be applied to the patch 415 and/or to the patient's skin 92 before applying the patch 415 in order to secure the controller 414 to the patient's skin 92. Such an adhesive may enhance acoustically coupling of the acoustic transducer(s) of the controller 414 to the patient's skin 92, and consequently to the implant 412 within the patient's body 94. Optionally, additional wetting material, including water, silicone oil, silicone gel, hydrogel, and the like, and/or other acoustically conductive material may be provided between the patch 415 or the acoustic transducer 422, and the patient's skin 92, e.g., to provide substantial continuity and minimize reflection or other losses and/or to secure the patch 415 to the patient.

Alternatively, the controller 414 may be carried by a belt (not shown) that may be secured around the patient, e.g., such that the acoustic transducer 422 is secured against the patient's skin. The belt may carry other components of the system 410, e.g., an external power supply for the controller 414. For example, a battery pack (not shown) may be carried by the belt that may be coupled to the controller 414 for providing electrical energy for its operation.

The patch 415 may be relatively light and compact, for example, having a maximum surface dimension (e.g., width or height) not more than about ten to two hundred millimeters (10-200 mm), a thickness not more than about five to one hundred millimeters (5-100 mm), and a weight not more than about twenty to four hundred grams (20-400 g), such that the controller 414 may be inconspicuously attached to the patient. Thus, the patient may be able to resume normal physical activity, without substantial impairment from the controller. Yet, the internal energy source of the controller 414 may be sufficiently large to communicate with the implant 412 for an extended period of time, e.g., for hours or days, without requiring recharging or continuous coupling to a separate energy source.

The system 410 may be used to control, energize, and/or otherwise communicate with the implant 412. For example, the controller 414 may be used to activate the implant 412. One or more external acoustic energy waves or signals 430 may be transmitted from the controller 414 into the patient's body 94, e.g., generally towards the location of the implant 412 until the signal is received by the acoustic transducer (not shown in FIGS. 3 and 4) of the implant 412. Upon excitation by the acoustic wave(s) 430 the acoustic transducer produces an electrical output that is used to close, open, or otherwise activate the switch (also not shown in FIGS. 3 and 4) of the implant 412. Preferably, in order to achieve reliable switching, the acoustic transducer of the implant 412 is configured to generate a voltage of at least several tenths of a volt upon excitation that may be used as an activation signal to close the switch, as described above.

As a safety measure against false positives (e.g., erroneous activation or deactivation), the controller 414 may be configured to direct its acoustic transducer 422 to transmit an initiation signal followed by a confirmation signal. When the acoustic transducer of the implant 412 receives these signals, the electrical circuit may monitor the signals for a proper sequence of signals, thereby ensuring that the acoustic switch of the implant 412 only closes upon receiving the proper initiation and confirmation signals. For example, the acoustic switch may only acknowledge an activation signal that includes a first pulse followed by a second pulse separated by a predetermined delay. Use of a confirmation signal may be particularly important for certain applications, for example, to prevent unintentional release of drugs by a drug delivery implant.

In addition to an activation signal, the controller 414 may transmit a second acoustic signal that may be the same as or different than the acoustic wave(s) used to activate the acoustic switch of the implant 412. Thus, the switch may be opened when the acoustic transducer of the implant 412 receives this second acoustic signal, e.g., by the acoustic transducer generating a termination signal in response to the second acoustic signal, in order to return the implant 412 to its sleep mode.

For example, once activated, the switch may remain closed indefinitely, e.g., until the energy storage device (not shown in FIGS. 3 and 4) of the implant 412 is completely depleted, falls below a predetermined threshold, or until a termination signal is received by the acoustic transducer of the implant 412 from the controller 414. Alternatively, the acoustic switch of the implant 412 may include a timer (not shown), such that the switch remains closed only for a predetermined time, whereupon the switch may automatically open, returning the implant 412 to its sleep mode.

Figure 5:
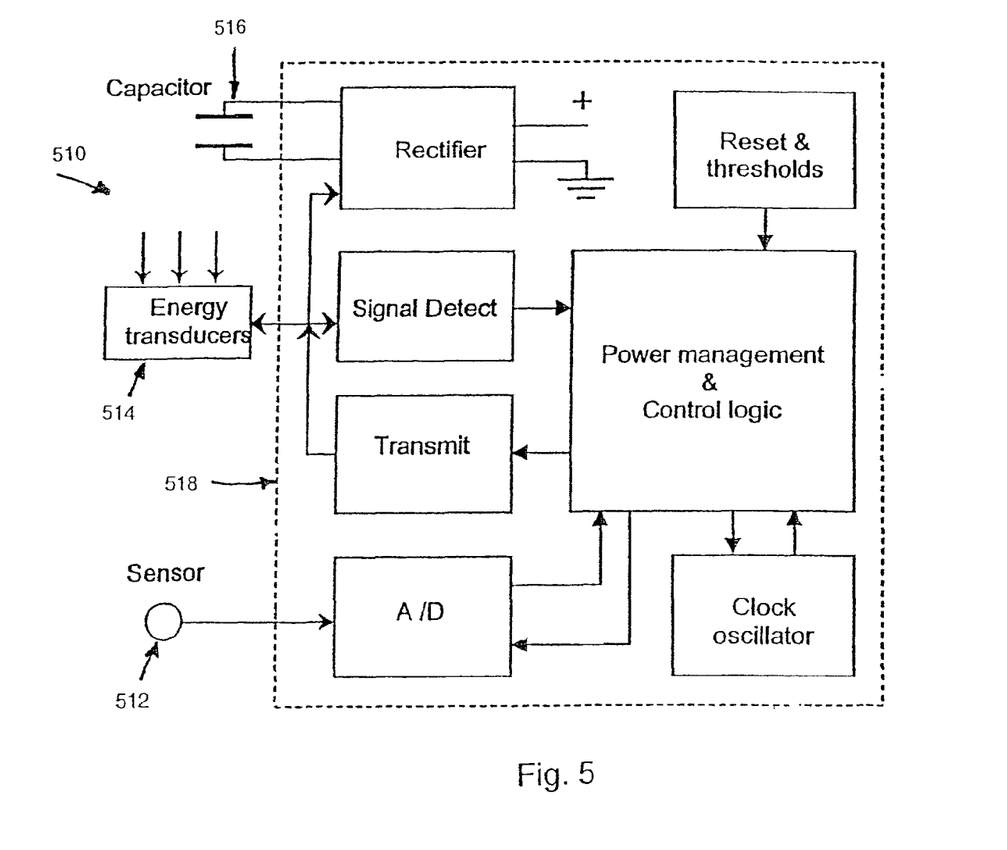
FIG. 5 is a schematic of another exemplary embodiment of an implant, in accordance with the present invention.

FIG. 5 shows an alternative embodiment of an implant 510 that does not include an acoustic switch. Generally, the implant includes a sensor 512, one or more energy transducers 514, one or more energy storage devices 516, and a control circuit 518, similar to the embodiments described above. The sensor 512 is preferably a pressure sensor for measuring intra-body pressure, such as an absolute variable capacitance type pressure sensor. In alternative embodiments, one or more other sensors may be provided instead of or in addition to a pressure sensor 512. For example, the sensor 512 may include one or more biosensors capable of measuring physiological parameters, such as temperature, electrical impedance, position, strain, pH, fluid flow, and the like. An external controller (not shown), such as that described above, may also be used to communicate with this implant.

Returning to FIG. 3, an external controller 414 in accordance with the present invention preferably has only sufficient power to control its own operation and to communicate with the implant 412. Because of its limited energy requirements, the controller 414 may be relatively small and portable, e.g., may be attached to the patient, while still allowing the patient to engage in normal physical activity. The controller 414 may be used to communicate with the implant 412, e.g., periodically activating or deactivating the implant 412, and/or recording data generated and transmitted by the implant 412. Because it is located outside the patient's body, the controller 414 may be more easily programmed or reprogrammed than the implant 412 itself, and/or may be repaired or replaced if necessary or desired.

In addition to the external controller 414, the system 410 may include one or more electronic devices 434 that may be coupled to the controller 414 via the interface 426, such as a recorder, a computer, a personal digital assistant, and/or a wireless device, such as a cellular telephone. The electronic device 434 may be directly coupled to the controller 414, by a connector or lead (not shown) extending from the patch 415 within which the controller 414 is provided. Alternatively, the controller 414 and/or patch 415 may include a wireless transmitter and/or receiver (not shown), e.g., a short-range RF transceiver, for communicating with the electronic device 434.

The electronic device 434 may be used to extract data from the memory 424 of the controller 414, e.g., sensor data and the like, received from the implant 412. This data may be included in a patient database maintained by health care professionals monitoring the patient receiving the implant 412.

In addition, the electronic device 434 may be used to program the controller 414, e.g., to program commands, timing sequences, and the like.

The system 410 may also include an external charger 416. For example, the implant 412 may include a rechargeable energy storage device (not shown in FIG. 3), preferably one or more capacitors, that are coupled to the acoustic transducer (also not shown in FIG. 3). The charger 416 may include a probe 428, including an acoustic transducer 430 for contacting a patient's skin 92. The charger 416 also includes a source of electrical energy 432, such as a radio frequency (RF) generator, that is coupled to the acoustic transducer 430. The charger 416 may also include electrical circuits for controlling its operation and buttons or other controls (not shown) for activating and/or deactivating the acoustic transducer 430.

The charger 416 may be used to charge or recharge the implant, e.g., periodically or before each activation. Because the charger 416 includes a substantially more powerful energy source than the controller 414, the charger 416 is generally a relatively bulky device compared to the controller 414, in particular due to the energy generator, which may be stationary or of limited mobility. In addition, the charger 416 may be used to recharge the controller 414 periodically, e.g., by a direct or wireless coupling. Alternatively, the controller 414 and patch 415 may be disposable, e.g., after its energy has been depleted, and replaced with another.

For purposes of comparison, an exemplary charger 416 may need to generate about ten kiloPascals (10 kPa) of acoustic energy for about twenty seconds (20 sec.) in order to fully charge the implant 412. In contrast, an exemplary controller 414 may be limited to outputting relatively smaller bursts of acoustic energy for communicating with, but not charging, the implant 412. Such acoustic signals may have a duration of as little as about one millisecond (1 ms), as opposed to the significantly longer charging signals generated by the charger 416.

The transducer 422 of the controller 414 may consume about one Watt (1 W) of power to produce a 1 kPa acoustic signal for about one millisecond. If the controller 414 communicates with the implant 412 on an hourly basis, the energy source 420 of the controller 414 may only need sufficient capacity to provide 0.024 Watt seconds per day (0.024 W·sec./day). Because of this low energy requirement, the energy source 420, and, consequently, the controller 414, may be relatively compact and portable, as compared to the charger 416. Thus, the energy source 420 may be self-contained within the controller 414, i.e., carried by the patch 415. Alternatively, a portable energy source, e.g., an external battery pack (not shown) may be provided for supplying electrical energy to the controller 414 that may be carried by the patient, e.g., on a belt (not shown).

In an alternative embodiment, the controller and charger may be provided as a single device (not shown), e.g., including one or more acoustic transducers and/or one or more processors for performing the functions of both devices, as described above. In this embodiment, the implant 412 may operate in a "half-duplex" mode, a quasi-continuous mode, or in a "full-duplex" mode, as described in the applications incorporated above.

It will be appreciated that the above descriptions are intended only to serve as examples, and that many other embodiments are possible within the spirit and the scope of the present invention.

What is claimed is:

1. A system for communicating with a medical device implanted within a patient's body, comprising:

one or more implants for placement within the body, each implant including an electrical circuit configured to perform one or more commands when the implant is activated, an energy storage device, an acoustic switch coupled between the electrical circuit and the energy storage device, and one or more acoustic implant transducers coupled to the acoustic switch, the one or more acoustic implant transducers configured for receiving an acoustic control signal to activate the acoustic switch between a first state, in which current is limited from flowing from the energy storage device to the electrical circuit, and a second state, in which current flows from the energy storage device to the electrical circuit;

an external controller for placement outside of the body, the external controller including one or more acoustic controller transducers for transmitting and receiving acoustic signals, wherein the transmitted acoustic signals include at least the acoustic control signal; and an external monitoring device in communication with the external controller, the external monitoring device configured to monitor one or more physiological parameters within the body.

2. The system of claim 1, wherein at least one of the one or more implants includes a biosensor coupled to the electrical circuit and adapted to sense a physiological parameter within the body.

3. The system of claim 2, wherein the at least one implant includes a transmitter, and wherein the implant is configured to transmit a data signal including sensor data from the biosensor to a device located outside of the body.

4. The system of claim 3, wherein the at least one implant is configured to transmit the sensor data to the external controller.

5. The system of claim 2, wherein the at least one implant is configured to transmit an acoustic data signal to the external controller, the acoustic data signal including sensor data from the biosensor.

6. The system of claim 5, wherein the external controller includes a processor for extracting the sensor data from the acoustic data signal.

7. The system of claim 5, wherein the external controller includes an interface for transferring the sensor data to the external monitoring device.

8. The system of claim 2, wherein at least one of the one or more implants includes an actuator coupled to the switch and a therapeutic device implanted within the body.

9. The system of claim 8, wherein the electrical circuit is configured to control the therapeutic device in response to a physiological parameter measured by the biosensor.

10. The system of claim 1, wherein at least one of the one or more implants includes an actuator coupled to the switch and a therapeutic device implanted within the body.

11. The system of claim 10, wherein the electrical circuit is configured to control the therapeutic device in response to an acoustic signal received from the external controller.

12. The system of claim 1, wherein the external monitoring device includes a patient database for monitoring the patient.

13. The system of claim 1, wherein the external monitoring device includes a means for programming the external controller.

14. A system for communicating with a medical device implanted within a patient's body, comprising:

one or more implants for placement within the body, each implant including an electrical circuit configured to perform one or more commands when the implant is activated, an energy storage device, an acoustic switch coupled between the electrical circuit and the energy storage device, and one or more acoustic implant transducers coupled to the acoustic switch, the one or more acoustic implant transducers configured for receiving an acoustic control signal to activate the acoustic switch between a first state, in which current is limited from flowing from the energy storage device to the electrical circuit, and a second state, in which current flows from the energy storage device to the electrical circuit, wherein at least one of the one or more implants includes a biosensor adapted to sense one or more physiological parameters within the body;

an external controller for placement outside of the body, the external controller including one or more acoustic controller transducers configured to receive an acoustic data signal transmitted from the at least one implant, the acoustic data signal including sensor data received from the biosensor, wherein the one or more acoustic controller transducers are configured to transmit acoustic signals, the transmitted acoustic signals including the acoustic control signal; and an external monitoring device in communication with the external controller, the external monitoring device configured to monitor the sensor data received from the biosensor.

15. The system of claim 14, wherein the external controller includes a processor for extracting the sensor data from the acoustic data signal.

16. The system of claim 14, wherein the external controller includes an interface for transferring the sensor data to the external monitoring device.

17. The system of claim 14, wherein at least one of the one or more implants includes an actuator coupled to the switch and a therapeutic device implanted within the body.

18. The system of claim 17, wherein the electrical circuit is configured to control the therapeutic device in response to a physiological parameter measured by the biosensor.

19. The system of claim 14, wherein the external monitoring device includes a patient database for monitoring the patient.

20. A system for communicating with a medical device implanted within a patient's body, comprising:

one or more implants for placement within the body, each implant including an electrical circuit configured to perform one or more commands when the implant is activated, an energy storage device, an acoustic switch coupled between the electrical circuit and the energy storage device, and one or more acoustic implant transducers coupled to the acoustic switch, the one or more acoustic implant transducers configured for receiving an acoustic control signal to activate the acoustic switch between a first state, in which current is limited from flowing from the energy storage device to the electrical circuit, and a second state, in which current flows from the energy storage device to the electrical circuit, wherein at least one of the one or more implants includes a biosensor adapted to sense one or more physiological parameters within the body;

an external controller for placement outside of the body, the external controller including one or more acoustic controller transducers configured to receive an acoustic data signal transmitted by the at least one implant, and a processor configured to extract sensor data from the biosensor, wherein the one or more acoustic controller transducers are configured to transmit acoustic signals, the transmitted acoustic signals including the acoustic control signal; and a patient management database adapted to store the extracted sensor data from the biosensor.

* * * * *